United States Patent [19]

Conrad

[11] 4,323,784

[45] Apr. 6, 1982

[54] DIAGNOSTIC RADIOLOGY APPARATUS FOR PRODUCING LAYER IMAGES

[75] Inventor: Bernhard Conrad, Erlangen, Fed. Rep. of Germany

[73] Assignee: Siemens Aktiengesellschaft, Berlin & Munich, Fed. Rep. of Germany

[21] Appl. No.: 141,059

[22] Filed: Apr. 17, 1980

[30] Foreign Application Priority Data

May 16, 1979 [DE] Fed. Rep. of Germany ....... 2919810

[51] Int. Cl.³ .............................................. A61B 6/00
[52] U.S. Cl. ............................ 250/445 T; 250/361 R
[58] Field of Search ........................... 250/445 T, 361

[56] References Cited

U.S. PATENT DOCUMENTS

| | | | |
|---|---|---|---|
| 4,065,397 | 5/1981 | Ruhrnschopf et al. ......... | 250/445 T |
| 4,247,774 | 1/1981 | Brooks ............................ | 250/445 T |
| 4,260,895 | 4/1981 | Schittenhelm .................. | 250/445 T |

Primary Examiner—Alfred E. Smith
Assistant Examiner—T. N. Grigsby
Attorney, Agent, or Firm—Hill, Van Santen, Steadman, Chiara & Simpson

[57] ABSTRACT

In an exemplary embodiment, a measuring arrangement for irradiating the radiography subject from different directions comprises a radiation source which emits a radiation beam which penetrates the layer to be examined, its dimension perpendicular to the layer plane being equal to the layer thickness, and a radiation receiver supplies electrical output signals which correspond to the radiation intensity measured. A computer calculates, from the output signals, the attenuation values of specific image points of the irradiated body layer. Correction devices are provided in the radiation beam with which the radiation quality (mean energy) of the radiation impinging on the receiver is determined, each preferably comprising several detectors arranged in series in the direction of radiation and separated from one another by a luminescent layer. The output signals of the correction detectors serve to correct for the radiation hardening in the patient. Correction detectors according to the disclosure are particularly suitable for use in apparatus with which fluoroscopic layer images capable of being evaluated in medical diagnosis are produced.

1 Claim, 4 Drawing Figures

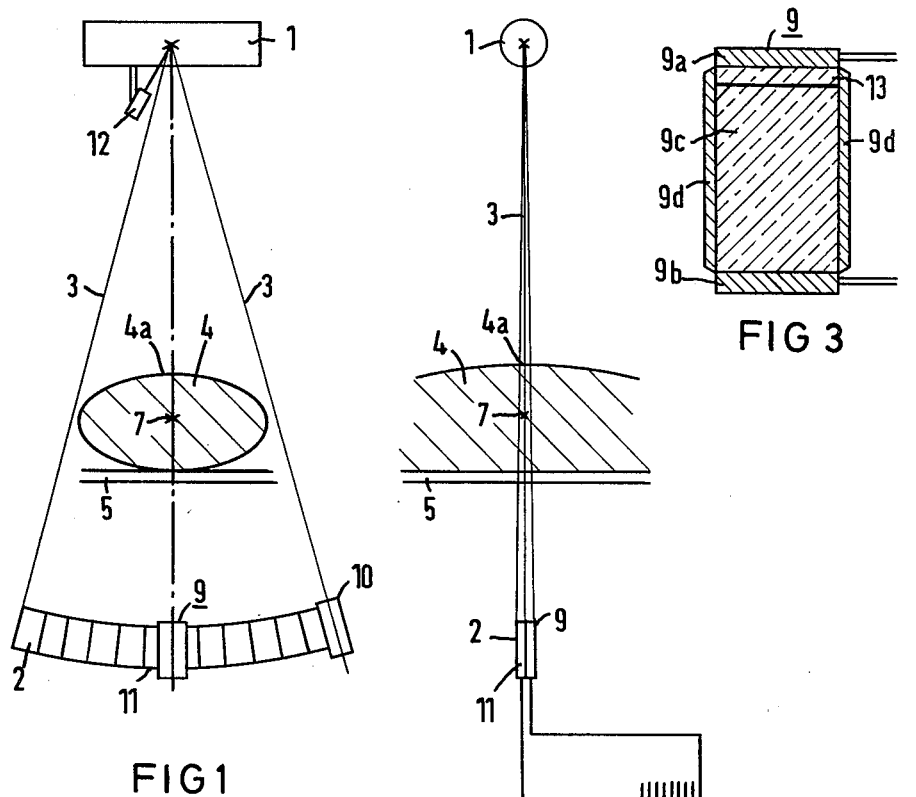
FIG 1
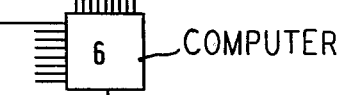
FIG 2
FIG 3
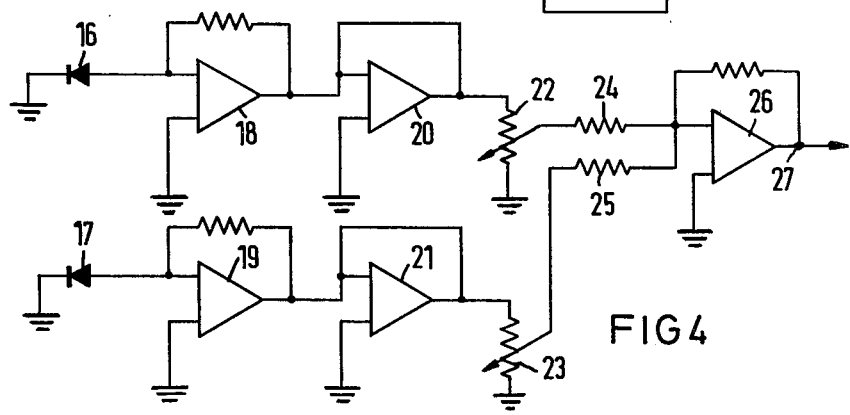
FIG 4

DIAGNOSTIC RADIOLOGY APPARATUS FOR PRODUCING LAYER IMAGES

BACKGROUND OF THE INVENTION

The invention relates to a diagnostic radiology apparatus for producing layer images of a radiography subject with a patient support, having a measuring arrangement for irradiating the radiography subject from different directions, comprising a radiation source which emits a radiation beam which penetrates the layer to be examined, and a radiation receiver which is located behind the radiography subject relative to the source and which supplies electrical output signals corresponding to the radiation intensity measured, and having a computer connected thereto for calculating from the output signals of the radiation receiver the attenuation values of image points of the body layer irradiated. An apparatus of this type is described in U.S. Pat. No. 4,065,397.

Known diagnostic radiology apparatus of this type, so-called computer tomographs, have x-rays tubes as radiation sources. They emit a Bremsstrahlen spectrum with wide spectral distribution. Even after normal preliminary filtration, this is still so wide that when the patient is irradiated there is a hardening of the rays which is dependent upon the thickness and the composition of the object irradiated. For producing an image from the output signals of the radiation receiver, as a result of this variable hardening of the rays which occurs in the body of the radiography subject, (1) in the interest of uniformity of the image and above all for a quantitative image evaluation, correction must take place in accordance with this hardening, (2) variable energy dependency of the radiation detectors must either be avoided or likewise be corrected, and (3) fluctuations in the average energy of the spectrum emitted from the radiation source (inclusive of preliminary filtration) must either be kept sufficiently small or likewise be corrected.

According to a prior patent application (corresponding to German Pat. No. 28 31 038.5) a rule is specified according to which a diagnostic radiology apparatus of the above-mentioned type is constructed such that the radiation quality within the radiation receiver or in its immediate vicinity can be measured, with the result that the corrections described can be made accurately.

In a development of the invention according to prior patent application and Pat. No. 28 31 038.5, the invention is based on the fact that when a single absorption body is used, the measurement results are still always dependent upon the radiation hardness derived from the correction detectors which output is also dependent on said radiation hardness.

This is obtained according to the prior patent application (and Pat. No. 28 31 038.5) in that there are provided, in the correction detectors, absorbers for the radiation, connected in series therewith, with the result that the average radiation energy of the radiation received can be determined from the output signals of these detectors. The output signals of these detectors depend on the quality of the radiation received in each case with the result that this quality can be determined from them. Therefore, they can be used to correct the measured signals.

It is true that U.S. Pat. No. 4,065,397 already describes a diagnostic radiology apparatus of the above-mentioned type where there is correction of the type described above; however, with this known diagnostic radiology apparatus this correction is made by a function stage wherein the correction function is stored. The respective radiation quality is not measured.

SUMMARY OF THE INVENTION

In a further development of the invention according to the prior patent application, the object underlying the present invention is to provide, in the case of a diagnostic radiology apparatus according to the introductory part of claim 1, an arrangement wherein a dependency of the sensitivity of the detectors on the hardness of the radiation is largely eliminated. This object is achieved in terms of the invention by the measures specified in the characterizing part of this claim.

In this respect, the invention is based on detector types wherein luminescent crystals are coordinated to the actual detectors, for example photodiodes. This can take place, for example, in such a way that a cesium iodide (CsI) crystal is cemented to a photodiode. As a result, the portion of the rays absorbed in this crystal is converted into light, which contributes to the measured value in addition to the rays which are absorbed in the diode. In this respect, ideally, the photoelectric current of these elements which occurs behind the patient would be proportional to the x-ray intensity. However, in practice, as already indicated above, for several reasons this is not the case.

For the variable energy dependency various effects enter into consideration. Owing to the extreme accuracy of measurement required however, these cannot be isolated in the experiment; with a few it can be estimated that they play a role. Effects to which a disruptive influence can be reliably attributed on the basis of measured tolerances in conjunction with estimations are as follows:

Variable crystal thickness. Variable "pre-absorption" by reflector lacquer coatings or layers and variable housing thickness at the inlet. Variable scattered radiation from the lacquer layers and from the housing from the side (its own and that of the adjacent detector), and in fact occasioned by variable layer thicknesses or inclination of the elements. Variable light conduction in the elements.

Owing to imperfect light conduction in the luminescent crystal, the signal of the photodiode varies according to the absorption point of the x-ray quantum. After measurement at a row of elements, on average between 90% and 100% (the signal with absorption immediately in front of the photodiode being arbitrarily set 100%). However, this progression in turn deviates from element to element, according to the Q-factor (quality) of the light conversion, between 93 . . . 100% and 87 . . . 100%. When the radiation hardens, the absorption center of gravity is displaced and consequently the signal of the elements changes to a greater degree with a steeper progression of the light conversion. This description with the aid of the absorption center of gravity is a simplification. In actual fact, the energy release must be viewed as a function of the place of absorption and must then be integrated with the light conversion as weighting function for the different radiation qualities.

With the above deviation by ±3% in the light conversion from the upper side of the crystal (radiation entry side), after prior calibration in air after hardening through 36 mm aluminum, the result is then that the signals differ by ±2°/00. (This hardening effect is approximately twice as great as is to be expected in the case of the cranium, it would be approximately ±1°/00 there.)

Deviation of the signal change as a result of variable light conduction is with ±2°/00 a great deal less than the deviation as a result of all the effects together; this is as great as ±3.5°/00, and in individual extreme cases as great as ±7°/00.

According to the invention however, this effect can be exaggerated and can be utilized for balancing in the following manner:

The crystal is provided with a photodiode on the radiation entry and exit side. It could then be expected that in the first instance for both diodes in the case of one element there would be a difference in the gradient of the characteristic curve of ±10% compared with ±3% in the case of the different elements, namely the signal of the diode on the radiation exit side increases with hardening, that of the diode on the radiation entry side diminishes as a result of displacement of the absorption center of gravity. However, an even greater difference can be expected since the upper diode does not act as light reflector, the characteristic curve must therefore take a steeper course than in the case of the elements having only one diode.

Measurement of a few elements having two diodes has produced a mean difference for signal hardening with 26 mm aluminum of 3%, hence ±1.5%.

The opposite displacement of the signals of the two diodes is thus twice as great as the deviation produced by the other effects. Appropriate mixing of the signals for the purpose of a weighted addition, in the case of each detector with individual adjustment of the mixing ratio, therefore allows all the elements to be adjusted to the same energy dependency. This can take place by the image-forming computer if twice the number of measuring channels than normal is used. In the case of calibration with and without radiation hardening it is possible to determine the individual "action" of the two respective diodes of a detector element. If $S_1$, $S_2$ are used to denote the signals of the diodes on the radiation entry and radiation exit side, respectively, and if $q_1$, $q_2$ are used to denote weighting factors between zero and one (0 and 1), then the combined signal $S_K$ is:

$$S_K = q_1 S_1 + q_2 S_2 \quad (1)$$

(cf. equations 2, 2a and 2b)

According to the measurement results hitherto available, it is sufficient to set $q_2 = 1$ and to compensate the individual deviation of the energy dependency of $S_2$ by different portions of the opposite signal $S_1$ ($q_1 = 0 \ldots 1$). However, greater possibilities for compensation result if, in addition, $q_2$ can be varied.

It is possible to avoid using twice the number of measuring channels if a summing device is connected to the two detectors which are connected before and after a luminescent crystal. As a result, a signal is obtained from both the detectors belonging to one crystal respectively, which can be further processed in a conventional manner.

Details of the invention also emerge from the subclaims.

Further details and advantages of the invention are further explained in the following with the aid of exemplary embodiments represented in the accompanying drawing sheet; and other objects, features and advantages will be apparent from this detailed disclosure and from the appended claims.

BRIEF DESCRIPTION OF THE DRAWINGS

FIG. 1 shows a diagnostic radiology apparatus with a view of detectors arranged in series as seen in the plane of the fan-shaped beam;

FIG. 2 shows a view of the arrangement according to FIG. 1 which view is taken at right angles to the plane of FIG. 1;

FIG. 3 shows a radiation receiver which is used in the diagnostic radiology apparatus according to FIGS. 1 and 2 as a detector for correction signals; and FIG. 4 shows a circuit arrangement for reducing the number of measuring channels.

DETAILED DESCRIPTION

FIG. 1 shows an x-ray tube 1 as radiation source, which forms a measuring arrangement with a radiation receiver 2. The x-ray tube 1 emits a fan-shaped x-ray beam 3, its dimension in the plane of the transverse layer 4a to be examined of a patient 4 lying on a support 5 being so great that the entire layer 4a to be examined is penetrated by x-radiation. The dimension of the x-ray beam 3 perpendicular to the layer 4a (as viewed in FIG. 2) is equal to the layer thickness.

The radiation receiver 2 comprises a row of individual detectors, for example 256 detectors, each of which supplies a signal which corresponds to the intensity of the x-radiation received. The detectors of the radiation receiver 2 are connected to a computer 6 which calculates from the output signals of the detectors of the radiation receiver 2, which are formed during rotation of the measuring arrangement 1, 2 through an angle of 360° about the axis of rotation 7, the attenuation values of specific image points of the layer 4a and hence an image of the irradiated cross section 4a of the patient 4. This image is reproduced on a display unit 8. In order to reduce the radiation to which the patient is exposed, the x-ray tube 1 can be pulsed during a scanning operation with the result that, for example, one set of output signals of the radiation receiver 2 is produced per degree of angle of rotation of the measuring arrangement. In the case of the example, 360×256 output signals are thereby produced.

In order to determine the radiation hardening in the patient 4, two correction receivers 9 and 10 are provided in the example. FIG. 2 shows a typical (non-correction type) detector 11 of the radiation receiver 2. The correction receiver 9 is disposed laterally at the side of this detector 11 as shown in FIG. 2. In accordance with FIG. 3, the correction receiver 9 comprises individual detectors 9a and 9b which, viewed in the direction of radiation, are arranged in series and are separated from one another by a luminescent layer 9c. The luminescent layer 9c attenuates the radiation received as a function of the radiation quality and hence also of the hardening of the radiation in the patient 4. The output signals of the detectors 9a and 9b are thus a measure of the energy distribution in the primary spectrum and, when the patient is brought in, also for the radiation hardening in the patient 4. They are supplied to the computer 6 for determining and effecting correction. Similarly, the output signals of the correction receiver 10, which likewise comprises individual detectors (as in FIG. 3) which are separated from one another by absorber layers, are supplied to the computer 6 for hardening correction of the signals supplied by the detectors of the radiation receiver 2.

In the example, two correction receivers 9 and 10 are provided which are distributed over the radiation receiver 2 in such a way that, in the case of the present medical subjects they permit virtually sufficient information regarding the spectrum over the entire breadth of the radiation receiver 2.

For checking the average energy of the radiation emitted from the x-ray tube 1 provision is made for a measuring probe 12 which is mounted at the outer periphery of the x-ray beam 3 and which continuously registers the radiation which is not affected by the absorption in the patient.

As a modification of the example according to FIGS. 1 and 2 it is conceivable to replace one or more detectors of the radiation receiver 2 by correction receivers 9 and 10 according to FIG. 3. In this case, the signal required to reconstruct the image can be obtained by adding up the output signals of the individual detectors 9a and 9b of a correction receiver 9, 10, etc. At the same time, correction factors for the energy displacement of the x-radiation can be formed from the differences between the signals of the individual detectors of the correction receivers.

In order to avoid using twice the number of measuring channels, it is possible to achieve the object by means of the circuitry shown in FIG. 4. The signal of the two diodes 16 and 17 corresponding to 9a and 9b of FIG. 3 of a detector element (photoelectric current) is firstly current-voltage converted in a conventional converter 18, 19. After an impedance converter 20, 21, any partial amount of this voltage can be tapped at the potentiometers 22, 23 by way of resistances. These component voltages are added in a summer 24, 25, 26. The sum voltage at the point 27 is then integrated as normal, analog-to-digital converted and processed in the computer.

Balancing is as follows: with potentiometer 22 at "max", potentiometer 23 at "zero" the signals are measured and stored, with radiation hardening of all the diodes, on one side of the elements; with potentiometer 22 at "zero", potentiometer 23 at "max" the signals of the diodes on the other side are measured and stored, in each case after prior calibration in the air. These measured values produce the necessary adjustment of the potentiometers in accordance with equation (1) or it can be determined from the computer by a program, respectively. According to previous measuring data (see above) there is, namely, always a value $S_M$ which is lower than all the signals of the diodes on the radiation entry side and higher than all the signals on the radiation exit side. The coefficients $q_1$, $q_2$ of equation (1) can be determined accordingly, for example by the system of equations:

$$\frac{q_1}{q_2} = \frac{S_M - S_2}{S_1 - S_M} \quad (2a)$$

$$S_M = q_1 S_1 + q_2 S_2 \quad (2b)$$

This system of equations results from the fact that $S_M$ is intended to represent the center of gravity of the values $S_1$ and $S_2$. The correspondingly mixed calibration factors for $S_1$, $S_2$ should then be used as calibration factor for calibration in the air.

It suffices in itself that the equation (2a), which requires that the signals are to weighted inversely to their difference from $S_M$ (mixing ratio), is satisfied and that the mixed signals of the different detectors thus obtained are calibrated with radiation in the air; subsequent calibration, which determines the changes in the measuring electronics and in the crystal, is also possible in this way. There is simply the secondary condition that the coefficients not be too great in order to supply signals still capable of being processed in the measuring electronics, and not too small in order that the signals can be processed undisturbed (in an interference-free fashion).

The photodiode 9a on the radiation entry side can be attached to the crystal 9c by a light guide 13, for example a small plate of plexiglass. For a crystal 9c which is 5 mm deep in the direction of radiation, an approximately 1 to 2 mm deep plate can be interposed as light guide 13 between photodiode 9a and crystal 9c. Any locally variable sensitivity of this photodiode 9a can thereby be prevented from causing any disturbances of the image which are produced as a result of inhomogeneities of the patient layer measured. As a result, the one side of the radiation entry face of the correction detector elements 9 and 10 can receive a different radiation intensity than the other. Variable local distributions of sensitivity of adjacent elements then lead to incorrect (erroneous) signal differences (in the absence of light guide 13). The greatest part of the radiation is absorbed in the luminescent crystal 9c immediately below its entry face. The light produced largely impinges in each case on the nearest point of the photodiode 9a. This means that objects which project only partially into the layer detected during scanning are detected as a signal by only a part of the photodiode. A light guide such as 13 effects, as a result of its depth and of the refraction of light thereby, a sufficiently "wide illumination" of the photodiode 9a. Local differences in sensitivity are thereby mitigated.

Losses of light can be at least reduced by providing the light guide 13 with a reflecting mass 9d on its lateral faces in the same way as the crystal 9c. With regard to the light conduction of each correction detector such as 9 and 10, the structure consisting of crystal 9c and reflector 9d then acts like a thicker crystal. The absorption of the composite structure including the light guide 13 essentially commences only at a greater depth where the cesium iodide of crystal 9c is present, in view of the lower atomic numbers and density of the plexiglass 13. This produces a reduction in the signal differences between the two diodes, because a portion of the light which would reach the photodiode 9a on the radiation entry side arrives at the other diode 9b as a result of scattering.

It will be apparent that many modifications and variations may be effected without departing from the scope of the novel concepts and teachings of the present invention.

I claim as my invention:

1. Diagnostic radiology apparatus for producing layer images of a radiography subject with a patient support, having a measuring arrangement for irradiating the radiography subject from different directions, comprising a radiation source which emits a radiation beam which penetrates the layer to be examined, the dimensions of said radiation beam perpendicular to the layer plane being equal to the layer thickness, and a radiation receiver which supplies electrical output signals which correspond to the radiation intensity measured, and having a computer connected to the radiation receiver for calculating from the output signals of the radiation receiver the attenuation values of specific points of the irradiated body layer, said radiation receiver comprising correction detector and absorber means for the radiation disposed in series such that output signals are supplied defining the mean radiation energy of the radiation receiver, characterized in that said correction detector and absorber means comprises an absorber in the form of a luminescent layer (9c) and at least two correction detectors (9a, 9b) arranged in series in the direction of radiation and separated from one another by the luminescent layer (9c), said luminescent layer converting the radiation received into light to which the correction detectors are sensitive characterized in that the correction detectors (9a, 9b) of said correction detector and absorber means (9) have respective correction detector outputs, and a summing circuit connected with said correction detector outputs and having an output channel for supplying a summation signal which is a function of the signals supplied by said correction detectors.

* * * * *